United States Patent
Keall et al.

(10) Patent No.: US 9,538,976 B2
(45) Date of Patent: Jan. 10, 2017

(54) MODULATING GANTRY ROTATION SPEED AND IMAGE ACQUISITION IN RESPIRATORY CORRELATED (4D) CONE BEAM CT IMAGES

(75) Inventors: Paul J. Keall, Greenwich (AU); Ricky O'Brien, Rozelle (AU); Benjamin J. Cooper, Chifley (AU); Jun Lu, Fayetteville, NY (US); Jeffrey F. Williamson, Richmond, VA (US)

(73) Assignees: The Board of Trustees of the Leland Stanford Junior University, Palo Alto, CA (US); The University of Sydney, Sydney, New South Wales ( * ) Notice: Subject to any disclaimer, the term of this patent is extended or adjusted under 35 U.S.C. 154(b) by 227 days.

(21) Appl. No.: 14/131,896

(22) PCT Filed: Jul. 27, 2012

(86) PCT No.: PCT/US2012/048693
§ 371 (c)(1),
(2), (4) Date: Jan. 9, 2014

(87) PCT Pub. No.: WO2013/016689
PCT Pub. Date: Jan. 31, 2013

(65) Prior Publication Data
US 2014/0192952 A1    Jul. 10, 2014

Related U.S. Application Data

(60) Provisional application No. 61/574,126, filed on Jul. 28, 2011, provisional application No. 61/671,028, filed on Jul. 12, 2012.

(51) Int. Cl.
*A61B 6/03* (2006.01)
*A61B 6/00* (2006.01)
*A61N 5/10* (2006.01)

(52) U.S. Cl.
CPC .......... *A61B 6/541* (2013.01); *A61B 6/4085* (2013.01); *A61B 6/486* (2013.01); *A61B 6/5205* (2013.01); *A61B 6/5264* (2013.01); *A61B 6/583* (2013.01); *A61N 2005/1061* (2013.01)

(58) Field of Classification Search
CPC ........ A61B 6/03; A61B 6/032; A61B 6/4085; A61B 6/486; A61B 6/541; A61B 6/5205; A61B 6/583; A61N 2005/1061
USPC ............................... 378/4, 8, 15, 19
See application file for complete search history.

(56) References Cited

U.S. PATENT DOCUMENTS

| 6,269,140 B1 | 7/2001 | Takagi et al. |
| 2005/0058248 A1 | 3/2005 | Klingenbeck-Regn et al. |
| 2005/0201509 A1* | 9/2005 | Mostafavi ............ A61B 5/1135 378/8 |

(Continued)

*Primary Examiner* — David E Smith
(74) *Attorney, Agent, or Firm* — Lumen Patent Firm

(57) ABSTRACT

A method of optimizing 4D cone beam computed tomography (4DCBCT) imaging is provided that includes using a scanner to generate projections of a target, where the projections are used to form a cone beam computed tomography (CBCT) scan of the target, where the CBCT includes a 3D image of the target, and using an appropriately programmed computer to control rotation speed of a gantry and projection acquisition of the CBCT in real-time according to a measured patient respiratory signal, where the real-time acquisition of the 4CBCT forms an optimized 4DCBCT image set.

9 Claims, 12 Drawing Sheets

(56) References Cited

U.S. PATENT DOCUMENTS

| | | | |
|---|---|---|---|
| 2006/0291615 A1 | 12/2006 | Nishide et al. | |
| 2008/0063137 A1 | 3/2008 | Hsieh et al. | |
| 2010/0142670 A1* | 6/2010 | Saito | A61B 6/032 378/8 |
| 2010/0322376 A1* | 12/2010 | Sendai | A61B 6/541 378/8 |
| 2012/0008744 A1* | 1/2012 | Bani-Hashemi | A61N 5/1047 378/65 |
| 2012/0039433 A1* | 2/2012 | Berkus | A61B 5/113 378/8 |

* cited by examiner

MODULATING GANTRY ROTATION SPEED AND IMAGE ACQUISITION IN RESPIRATORY CORRELATED (4D) CONE BEAM CT IMAGES

CROSS-REFERENCE TO RELATED APPLICATIONS

This application is a 371 of PCT/US2012/048693 filed on Jul. 27, 2012. PCT/US2012/048693 filed on Jul. 27, 2012 claims the benefit of US 61/574126 filed on Jul. 28, 2011 and US 61/671028 filed on Jul. 12, 2012.

STATEMENT OF GOVERNMENT SPONSORED SUPPORT

This invention was made with Government support under contract CA116602 awarded by the National Institutes of Health. The Government has certain rights in this invention.

FIELD OF THE INVENTION

The present invention relates generally to radiotherapy. More particularly, the invention relates to obtaining 4DCBCT images of the lungs and lung tumors using mathematical optimization models for Respiratory Motion Guided-4DCBCT (RMG-4DCBCT).

BACKGROUND OF THE INVENTION

Lung cancer is the leading cause of cancer related death worldwide (18%) with 1.2 million new cases reported annually. Despite 36% to 71% of lung cancer patients receiving radiotherapy, and continuous efforts to improve treatment outcomes, the 5-year survival rate is only 16%. These patients urgently need better treatment techniques and tools to improve survival rates.

An increase in tumor dose of 1-Gy results in a 4% improvement in survival. On the other hand, a 1-Gy decrease in overall mean lung dose results in a 2% reduction in pneumonitis. It is clear from these statistics that better targeted radiotherapy has the potential to improve treatments outcomes. Image-guided radiotherapy (IGRT) has been used to simultaneously increase tumor dose while minimizing the dose to the surrounding healthy tissue.

IGRT is used by more than 93% of radiation oncologists in the United States. However, imaging techniques such as MRI, PET, CT and CBCT are blurry or contain artifacts when there is significant respiratory motion. As a consequence, it is difficult for a radiotherapist to accurately position a lung tumor patient for treatment, which increases the likelihood that some of the radiation that is targeted at the tumor will irradiate healthy lung tissue.

FIG. 1a shows a diagram of the projection geometry for CBCT imaging showing the first (P1) projection and $i^{th}$ ($P_i$) projection. The gantry rotates around the target at a constant velocity with a constant pulse rate between projections. FIG. 1b shows a photograph of a linear accelerator used in radiotherapy with the on-board-imager.

Two of the most common imaging techniques used by radiotherapists for IGRT are CT and CBCT imaging. CT images are obtained by taking projections in a plane, or slice, then moving the gantry forward a small distance where the process is repeated. Once a number of slices have been taken across the anatomy the slices are reconstructed into a 3D image. Alternatively, some CT systems take projections in a continuous helical motion rather than using slices. CT images are usually of a higher quality when compared to CBCT images so CT imaging is usually used for diagnostic and treatment planning purposes. CBCT differs from CT in that the gantry, containing the X-ray source and detector, is rotated around the anatomy during which a series of cone shaped projections are taken (see FIG. 1b). The projections are then reconstructed using the Feldkamp-Davis-Kress (FDK) algorithm to give a 3D view of the patient's anatomy.

CBCT images can be obtained in the treatment room using the OBI's attached to linear accelerators and are used in the treatment room by radiotherapists to position their patients for treatment.

4DCT imaging provides a video, or movie, of the 3D geometry. The motion of the heart, abdomen, prostate, lungs and tumor can be observed over time. To acquire 4DCT images of the lungs, the respiratory cycle is separated into respiratory bins such as inhale limit, exhale limit and at different stages between the two limits. A full set of slices are collected in each respiratory bin so that a four dimensional view of the changing anatomy can be obtained. Two techniques are commonly used to acquire 4DCT images in practice: (1) Prospective where you wait until the patient's breathing is in the desired region then acquire a slice before moving the couch for the next slice and repeating the process. (2) Retrospective where you acquire data for all phases of the respiratory cycle by oversampling the dataset and then retrospectively allocating slices to respiratory bins.

It has been shown that lung tumors typically move 0.5 to 1 cm, and as much as 5 cm, during the breathing cycle. Artifacts are not entirely eliminated by 4DCT imaging. It has been observed that at least one artifact exists in 90% of 4DCT images of the diaphragm and heart. Despite the problems associated with respiratory motion, there has been a significant increase in 4DCT imaging since it was first published. In 2009, usage of 4DCT was over 44% in the United States with a continuous upwards trend.

CBCT images are obtained by taking between 120 and 600 evenly spaced projections. For each projection, a cone shaped beam is emitted by the source and the attenuation of the beam is recorded by the detector (see FIG. 1a). The gantry is rotated around the patient at a constant angular velocity, which for safety reasons is limited to 6°/s, and an X-ray pulse rate of around 0.2 seconds is used. Total imaging time can be around 1 or 2 minutes, which depends on the desired number of projections and the velocity of the gantry.

For smaller targets, such as arms, head and neck, it is possible to use full fan projections where the beam is the full cone shape. This can reduce imaging time as the gantry only needs to rotate 180° plus the angular width of the cone. In most practical applications, such as the abdomen, half fan projections are used where the gantry rotates the full 360°.

Once all of the projections have been collected, image reconstruction algorithms are used to reconstruct a 3D view of the target. The FDK algorithm is the most popular algorithm used to reconstruct images. Image reconstruction can be a slow process that can take several minutes to reconstruct a single image. Total Variation and Tight Frame methods have been implemented to reconstruct images using Graphics Processing Units (GPU's). In addition to the computation time improvements obtained using a GPU, these methods show promise at reducing the number of projections to below 100 and therefore reducing the radiation dose to the patient.

Image quality is better if the projections are evenly spaced in gantry angle; see the polar plot in FIG. 2a for an example of good projection spacing. However, when respiratory motion is involved, projections are taken at different stages during the respiratory cycle; see the polar plot in FIG. 2b where numbers (1), (2) and (3) are used to identify projections taken at inhale limit, exhale limit and mid inhale. The resulting image is likely to contain artifacts, or the image will be blurry, in the region where significant respiratory motion takes place.

4DCBCT imaging attempts to produce images showing the motion of the lungs, and tumor, during the breathing cycle. This is achieved by collecting a full set of projections in a number of respiratory bins; the projections in the polar plot of FIG. 2c give an example of projections taken only from the inhale limit respiratory bin. Within each respiratory bin, there is limited anatomical motion, so blurring and artifacts in the resulting images are reduced. Three-dimensional images are reconstructed in each respiratory bin and a video is created showing a 4D view of the anatomy. Commercial systems use a constant gantry angular velocity with a constant X-ray pulse rate and post-process projections into respiratory bins. However, as can be seen in the polar plot in FIG. 2c, if the gantry is rotated around the patient with a constant angular velocity the angular separation between projections is not ideal and projection clustering occurs.

There have been some attempts to handle respiratory motion by accounting for motion in the image reconstruction algorithms. Motion compensated CBCT uses estimates of respiratory motion to reconstruct an image. Taking this approach further, some researchers have attempted to modify the image reconstruction algorithms to look for a stationary component with a separate periodic component. These methods assume that the patient's breathing is regular so the algorithms are likely to have difficulty reconstructing an image if the patient's breathing is irregular.

One of the evolving image-guidance methods to account for lung cancer motion during each treatment session, with applications in liver, pancreas and other thoracic/abdominal malignancies, is $1^{st}$ generation four-dimensional cone beam computed tomography (4DCBCT). The projection images and respiratory signal are synchronously acquired and post-processed into respiratory correlated phase bins, such as end-inhale, mid-inhale, etc.

However, in the current implementation there is no communication between the respiratory signal and image acquisition. This results in bunched angular projections, with the CBCT images suffering from poor image quality and streak artifacts. The poor quality limits the use of current images for online guidance and anatomic and functional adaptation.

Common to all current 4DCBCT systems is the use of a constant angular velocity of the gantry. The gantry is rotated around the patient at a much slower rate than for 3DCBCT imaging. After the projections have been collected, they are compared with the recorded breathing trace and then post-processed into respiratory bins. The aim is to collect enough projections in each respiratory bin, with relatively even angular separation, to reconstruct an image. However, the use of a constant angular velocity results in clustering of projections.

As an example of projection clustering consider the left plot in the top row of FIG. 3a where a sinusoidal breathing wave is given for a patient with a 15 hz (cycles per minute) breathing rate.

FIGS. 3a-3d show examples of clustered and missing projections with a sinusoidal breathing pattern at 15 hz. In row (1) the patient's breathing wave is shown with displacement on the vertical axis and time on the horizontal axis where the breathing cycle is separated into 10 displacement bins. The percentages listed are the approximate percentage of time spent in each displacement bin. The (1), (2) and (3) vertical lines correspond to projections that are allocated to respiratory bins 1, 5 and 8 respectively. The polar plots show the gantry angles at the projections taken in respiratory bins 1 (1), 5 (2) and 8 (3) with a constant gantry velocity of 1:5°/s.

The x-axis tick marks of FIG. 3a correspond to the time at which a projection is taken if a pulse rate of 0.2 s is used. The projections corresponding to displacement bins 1, 5 and 8 are marked as (1), (2) and (3) respectively. If the gantry is rotated with an angular velocity of 1.5°/s and a projection is taken every 0.2 seconds there will be 1200 projections in total taken over 4 minutes. If the displacement bin at exhale limit is analyzed (1), then either 4 or 5 projections, with an angular separation of 0.9° to 1.2°, will be taken in the 0.82 seconds at exhale limit. The patient's breathing will not enter the exhale limit respiratory bin for a further 3.18 seconds in which time the gantry moves 4.77°. This process will be repeated with a cluster of 4 or 5 projections followed by a gap of at least 4.77° before the next cluster of projections. A polar plot showing the gantry angle for each projection in displacement bin 1 is the exhale limit (1) polar plot in FIG. 3b. In total there will be 240 projects in 60 clusters if 4 projections are taken per respiratory bin. In the worst case scenario there will be 5 projections per respiratory bin resulting in 300 projections in displacement bin 1.

Clustering of projections results in a higher radiation dose to the patient for a small improvement in image quality.

The (2) polar plot in FIG. 3c, for displacement bin 5, shows an example of missed projections. Even though the polar plot has an excellent angular separation between projections, only one projection exists per respiratory cycle. The patient has received a radiation dose from 60 projections but there are not enough projections to reconstruct an image of suitable quality. This problem occurs because only 0.13 seconds is spent in displacement bin 5 during inhale and a further 0.13 seconds during exhale. A 0.2 second projection pulse rate can miss the displacement bin altogether. In the example, a projection is taken during exhale but not during inhale. In practice the displacement bin can be missed during both inhale and exhale in consecutive cycles leading to large gaps between projections. In the worst case, the respiratory bin could be missed during both inhale and exhale resulting in no projections allocated to respiratory bin 5.

The polar plot (3) in FIG. 3d shows a situation that is between the polar plots (1) and (2). A projection is taken during both inhale and exhale, resulting in 120 projections in total, but the projections are unevenly spaced. For displacement bin 8 there may be enough projections to reconstruct an image, but if the projections were more evenly spaced fewer projections would be required to obtain an image with comparable quality.

Because projections are post-processed into respiratory bins, first generation methods are unable to adapt if the patient's breathing is irregular as no feedback with the patient's respiratory data is used to regulate the gantry. Therefore image quality is likely to be poor if the patient's breathing is irregular.

What is needed is a method that improves the angular separation of projections in each respiratory bin in real-time during 4DCBCT imaging.

SUMMARY OF THE INVENTION

To address the needs in the art, a method of optimizing 4D cone beam computed tomography (4DCBCT) imaging is provided that includes using a scanner to generate projections of a target, wherein the projections are used to form a cone beam computed tomography (CBCT) scan of the target, wherein the CBCT comprises a 3D image of the target, and using an appropriately programmed computer to control rotation speed of a gantry and projection acquisition of the CBCT in real-time according to a measured patient respiratory signal, wherein the real-time acquisition of the CBCT forms an optimized 4DCBCT image set.

According to one aspect of the invention, a time interval between projections of the CBCT is varied.

In a further aspect of the invention, the acceleration and velocity of the gantry are varied.

In another aspect of the invention, a breathing trace is used to optimize a projection schedule.

In yet another aspect of the invention, the optimized projection schedule includes regulating a gantry angle and regulating a projection pulse rate.

According to one aspect of the invention, the control of the gantry rotation speed and projection acquisition of the 4DCBCT in real-time includes using sensors to analyzing a patient's breathing pattern to determine a representative breathing trace, separating the patients representative breathing trace into a number of phase or displacement based respiratory bins, using mathematical optimization techniques on the computer to determine and apply a gantry angle and a projection pulse rate schedule from the representative breathing cycle, recomputing the gantry angle and a projection pulse rate schedule if the patient's breathing deviates from the representative breathing cycle, and continue the projection acquisition according to the recomputed gantry angle and projection pulse rate schedule.

In another aspect of the invention, where the motion of the gantry is regulated within specified limits, where the limits can include minimum and maximum velocity, minimum and maximum acceleration, minimum and maximum jerk, minimum and maximum time between projections, minimum and maximum number of projections, minimum and maximum number of projections per respiratory bin, maximum imaging radiation dose, minimum and maximum image quality, minimum and maximum probability on the robustness of the schedule to irregular breathing, minimum and maximum likelihood of reconstructing a suitable schedule when the patients breathing becomes irregular, minimum and maximum number of respiratory bins and total imaging time.

In a further aspect of the invention, the patient respiratory signal is used to modulate the speed of the gantry and modulate the projection acquisition to yield images for each phase of a breathing trace at a predetermined and optimized angular spacing. In one aspect optimizing the gantry angle includes operations that include minimizing the time required to acquire the 4DCBCT projections, minimizing the angular separation between the gantry angles for each projection, minimizing the root mean squared of the angular separation between the projections, maximizing the image quality in each respiratory bin, maximizing the number of images acquired, maximizing the number of respiratory bins, maximizing the likelihood of acquiring suitable quality images when the patients breathing becomes irregular, maximizing the robustness of the schedule, and minimizing the radiation dose to the patient.

DETAILED DESCRIPTION

Figure 1A:
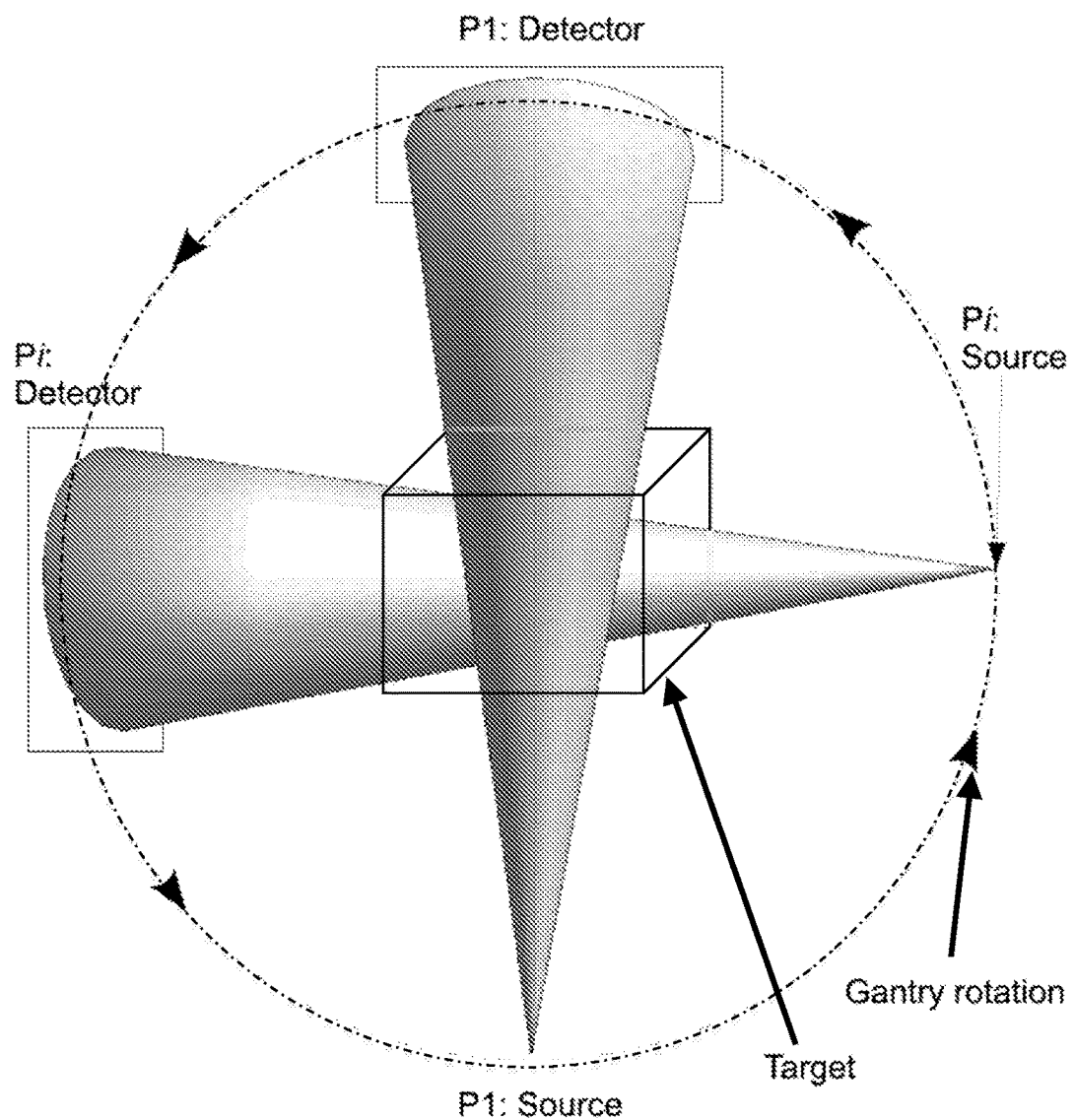
FIG. 1a shows a diagram of the projection geometry for CBCT imaging showing the first (P1) projection and $i^{th}$ (Pi) projection. The gantry rotates around the target at a constant velocity with a constant pulse rate between projections.
Figure 1B:
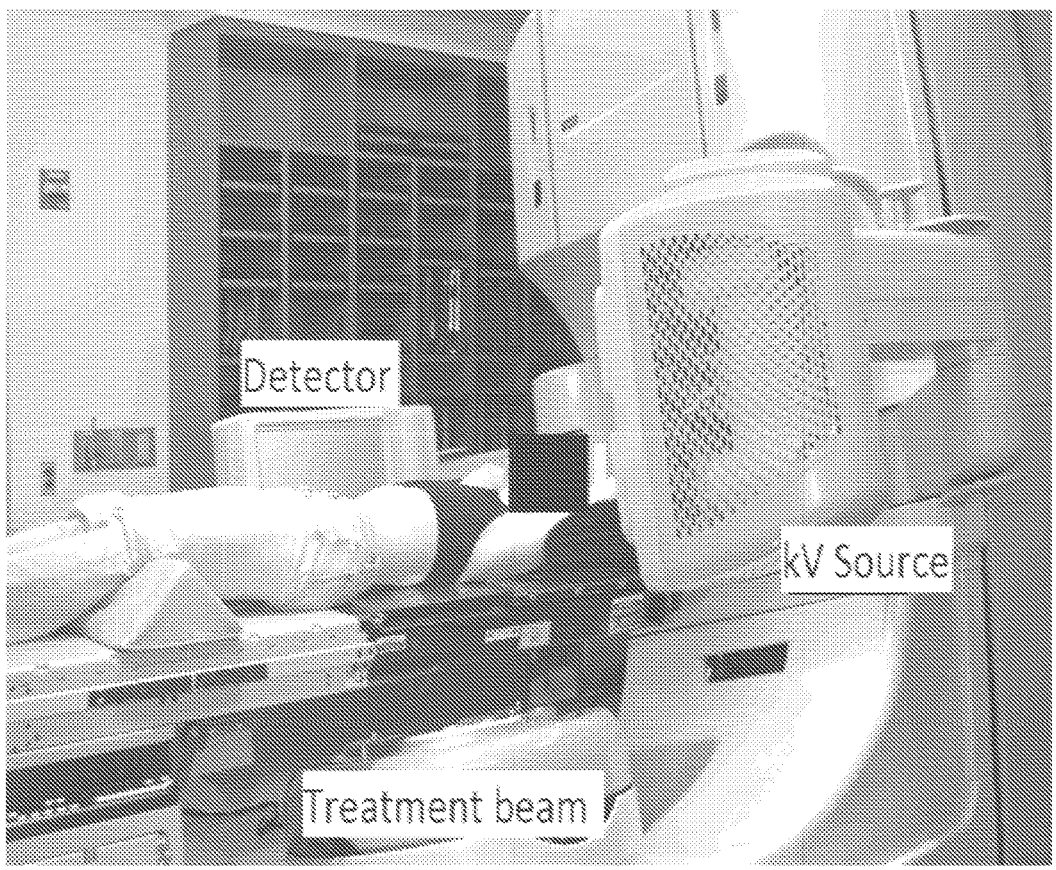
FIG. 1b shows an image of a linear accelerator used in radiotherapy with the on-board-imager.

Four Dimensional Cone Beam Computed Tomography (4DCBCT) images of lungs are rarely used by radiotherapists to position a patient for treatment because of blurring as a result of respiratory motion. One embodiment of the current invention provides a novel Mixed Integer Quadratic Programming (MIQP) model for Respiratory Motion Guided-4DCBCT (RMG-4DCBCT), which can be used to obtain 4DCBCT images of the lungs and lung tumors by a radiotherapist in the treatment room prior to treatment. RMG-4DCBCT regulates the gantry angle and projection pulse rate, in response to the patient's respiratory signal, so that a full set of evenly spaced projections can be taken in a number of phase, or displacement, bins during the respiratory cycle. In each respiratory bin, an image is reconstructed from the projections to give a 4D view of the patient's anatomy so that the motion of the lungs, and tumor, can be observed during the breathing cycle. A solution to the full MIQP model in a practical amount of time, 10 seconds, is not possible with the leading commercial MIQP solvers, so a heuristic method to generate an initial feasible solution and a k-opt-exchange heuristic to improve the initial feasible solution are presented. In a further embodiment, the heuristic method is used to generate the initial feasible solution, which has a computation time under one second, which significantly improves the angular spacing between projections compared to current 4DCBCT techniques. The strength of the current invention is that it allows, for the first time, a new projection schedule to be computed whenever the patient's breathing becomes irregular. Additional benefits of the current invention, over other 4DCBCT imaging techniques, include a reduction in the total number of projections and a reduction in the radiation dose because fewer projections are required to reconstruct an image when the angular separation between projections is more uniform.

One embodiment of the current invention provides a MIQP optimization model for RMG-4DCBCT that regulates the gantry angle and projection pulse rate with the aim of improving the angular separation between projections compared to existing 4DCBCT techniques. Unlike existing 4DCBCT methods, if the patient's breathing becomes irregular, the invention is able to rapidly re-optimize the projection sequence and continue image acquisition. An additional benefit of using the optimization model of the current invention is that, due to the more evenly spaced projections, fewer projections are required to produce good quality images. This results in a lower radiation dose to the patient compared to existing 4DCBCT techniques.

In one aspect optimizing the gantry angle includes operations that include minimizing the time required to acquire the 4DCBCT projections, minimizing the angular separation between the gantry angles for each projection, minimizing the root mean squared of the angular separation between the projections, maximizing the image quality in each respiratory bin, maximizing the number of images acquired, maximizing the number of respiratory bins, maximizing the likelihood of acquiring suitable quality images when the patients breathing becomes irregular, maximizing the robustness of the schedule, and minimizing the radiation dose to the patient.

Figure 2A:
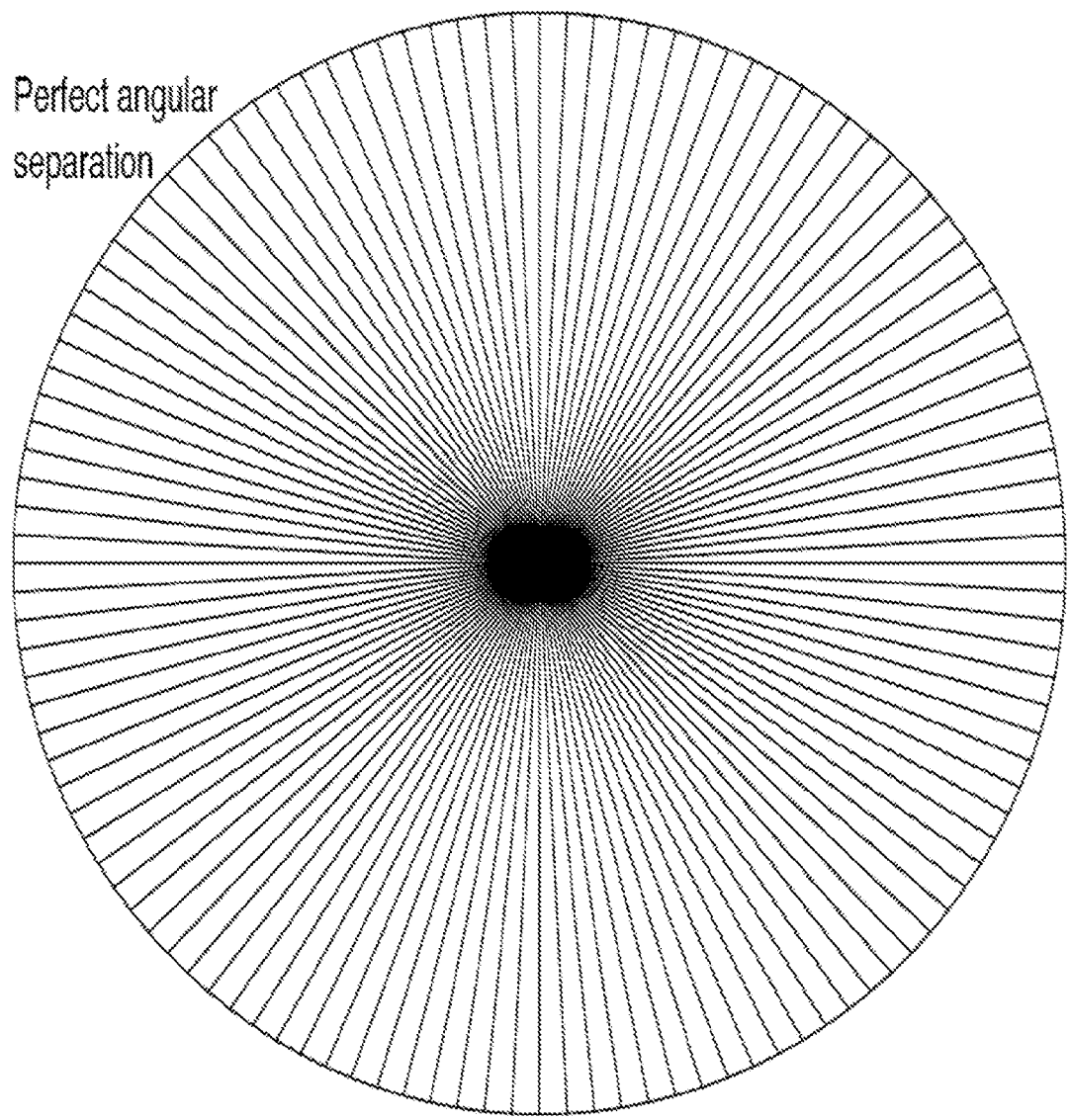
FIG. 2a-2c show a polar plot of the gantry angles for 120 evenly spaced projections, a polar plot of the gantry angles for 360 projections with the gantry moving at 5°/s, a projection taken every 0.2 seconds and the patient breathing sinusoidally at 15 cycles per minute, and gantry angles for projections corresponding to the inhale limit respiratory bin showing projection clustering, respectively. Projections taken while the patient's breathing was at inhale limit (top ⅓ of lung displacement) are marked as (1), mid inhale (middle ⅓ of lung displacement) are marked (2) and exhale limit (bottom ⅓ of lung displacement) are marked in (3).
Figure 2B:
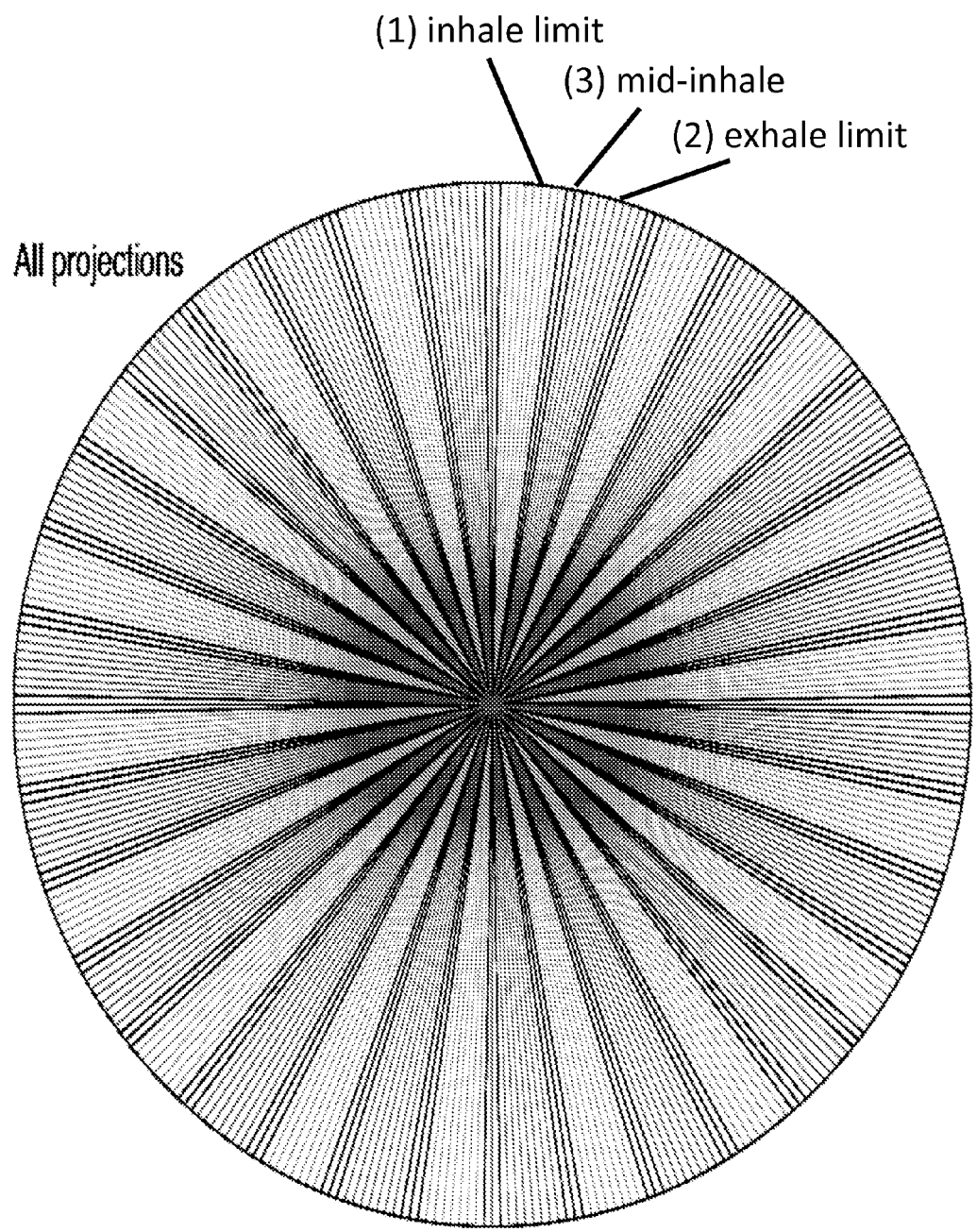
Figure 2C:
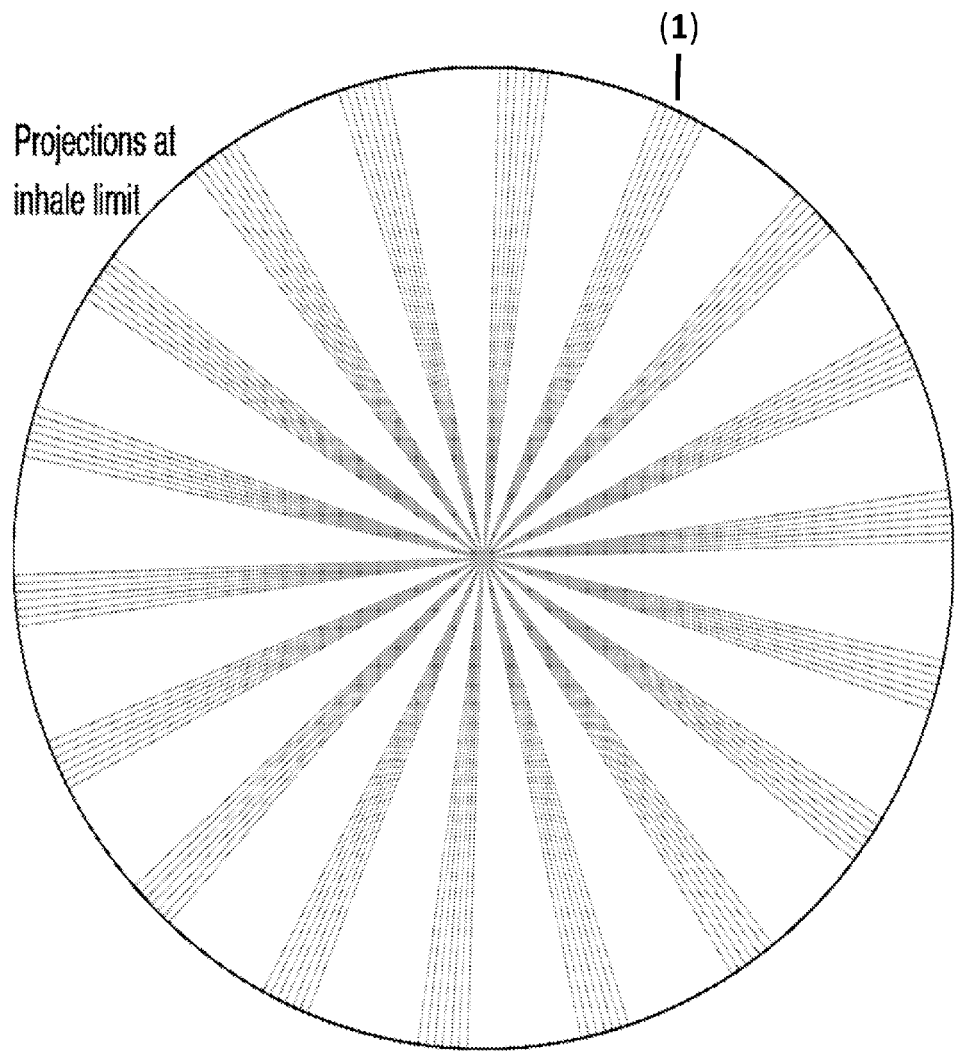
Figure 3A:
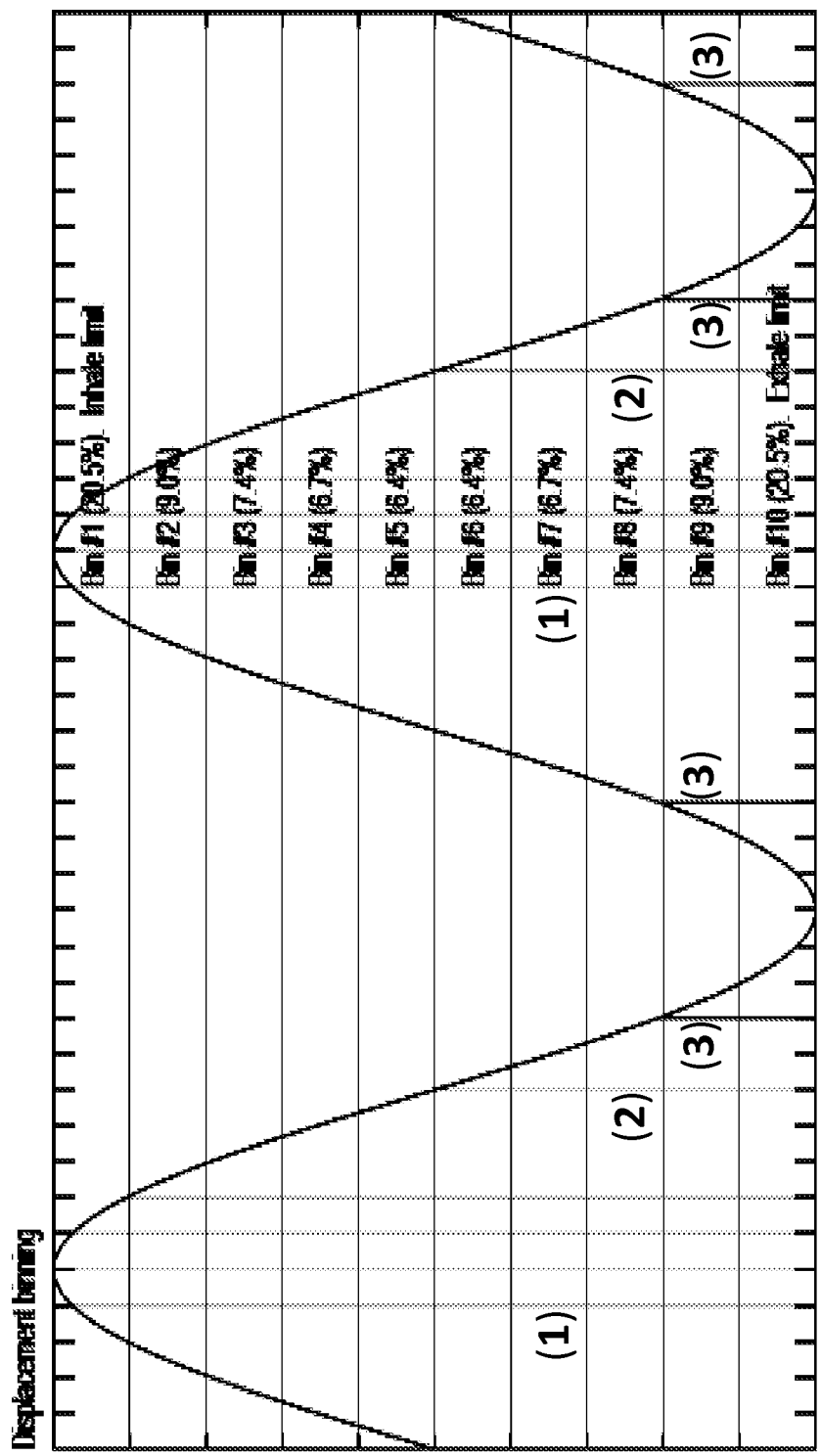
FIGS. 3a-3d show examples of clustered and missing projections with a sinusoidal breathing pattern at 15 hz.
Figure 3B:
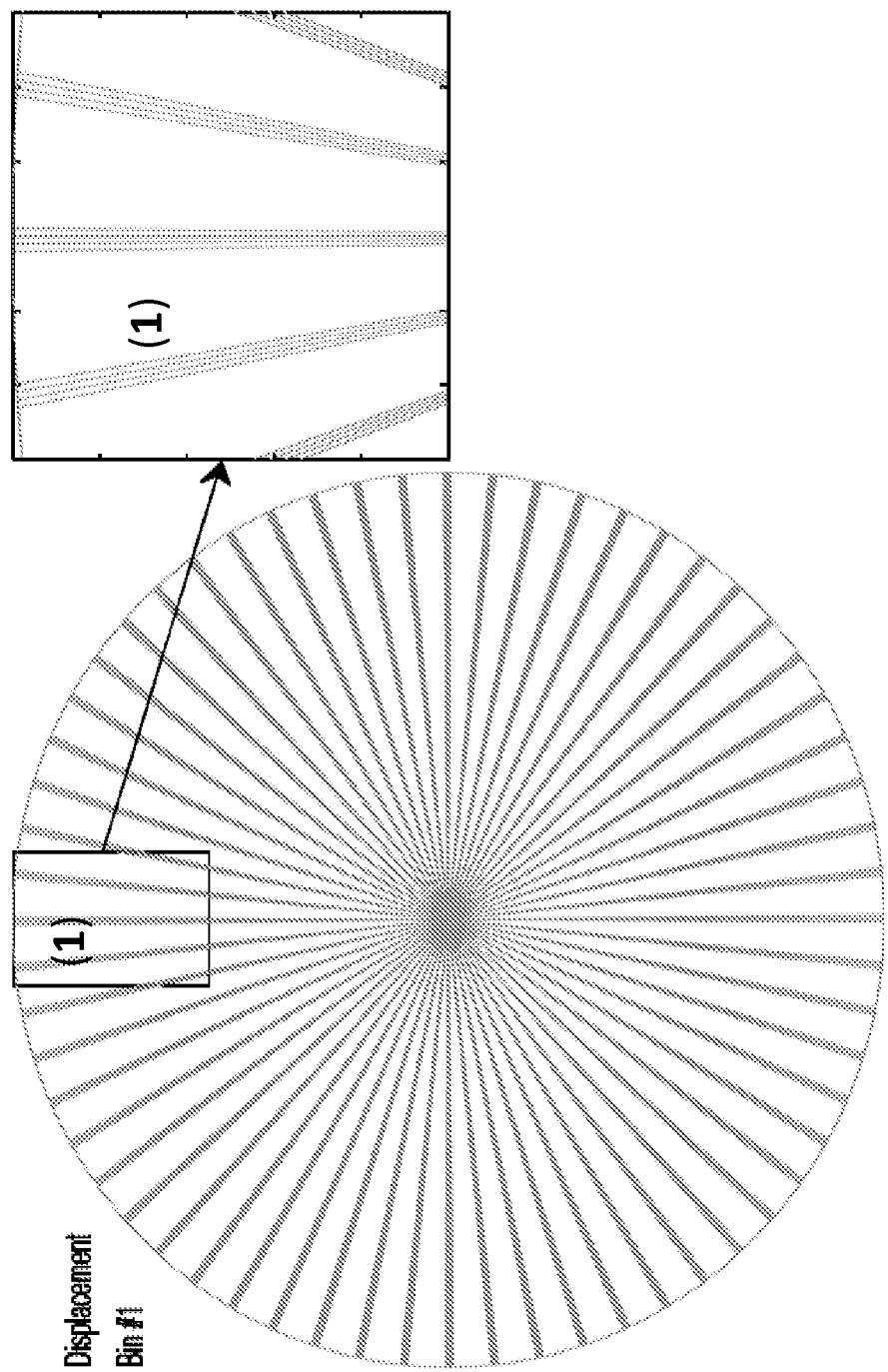
Figure 3C:
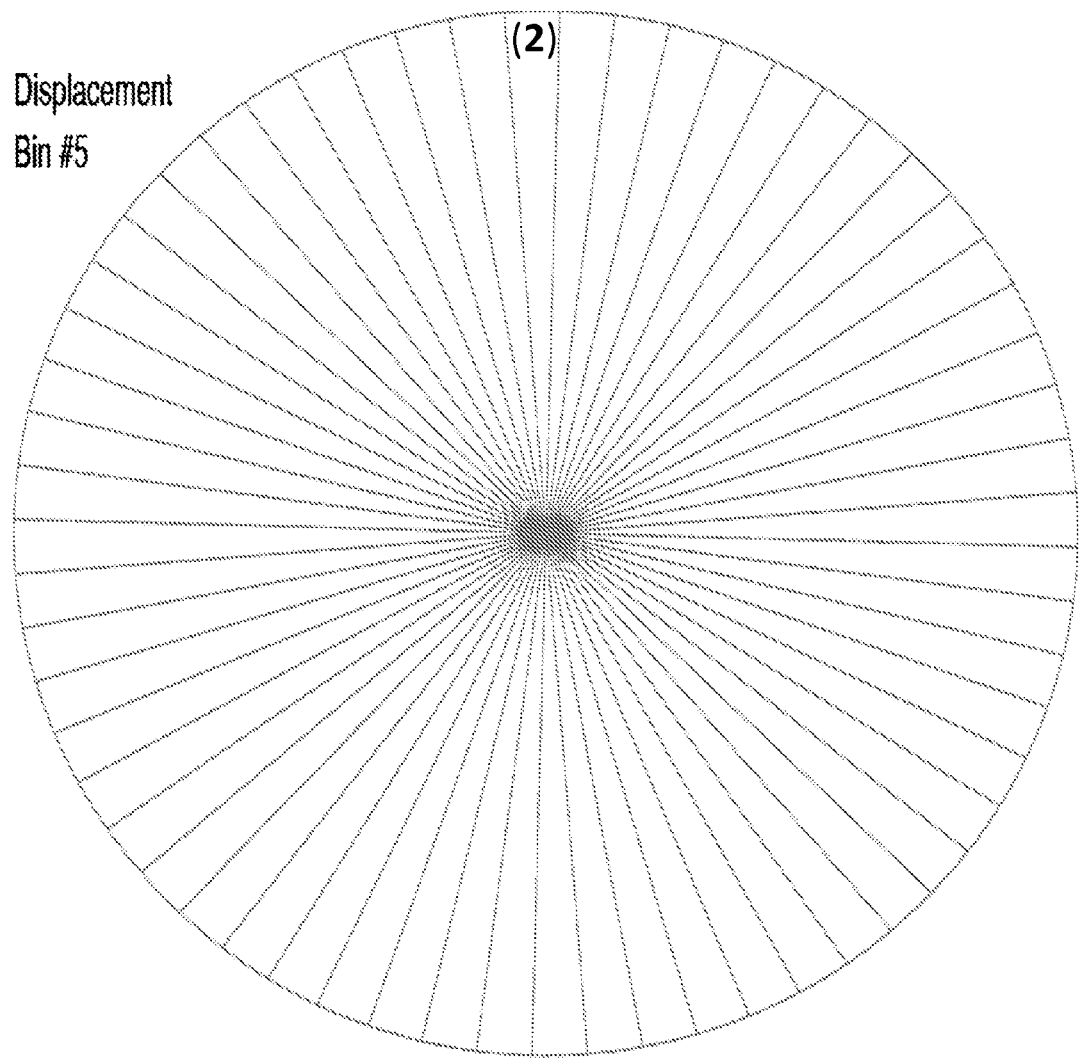
Figure 3D:
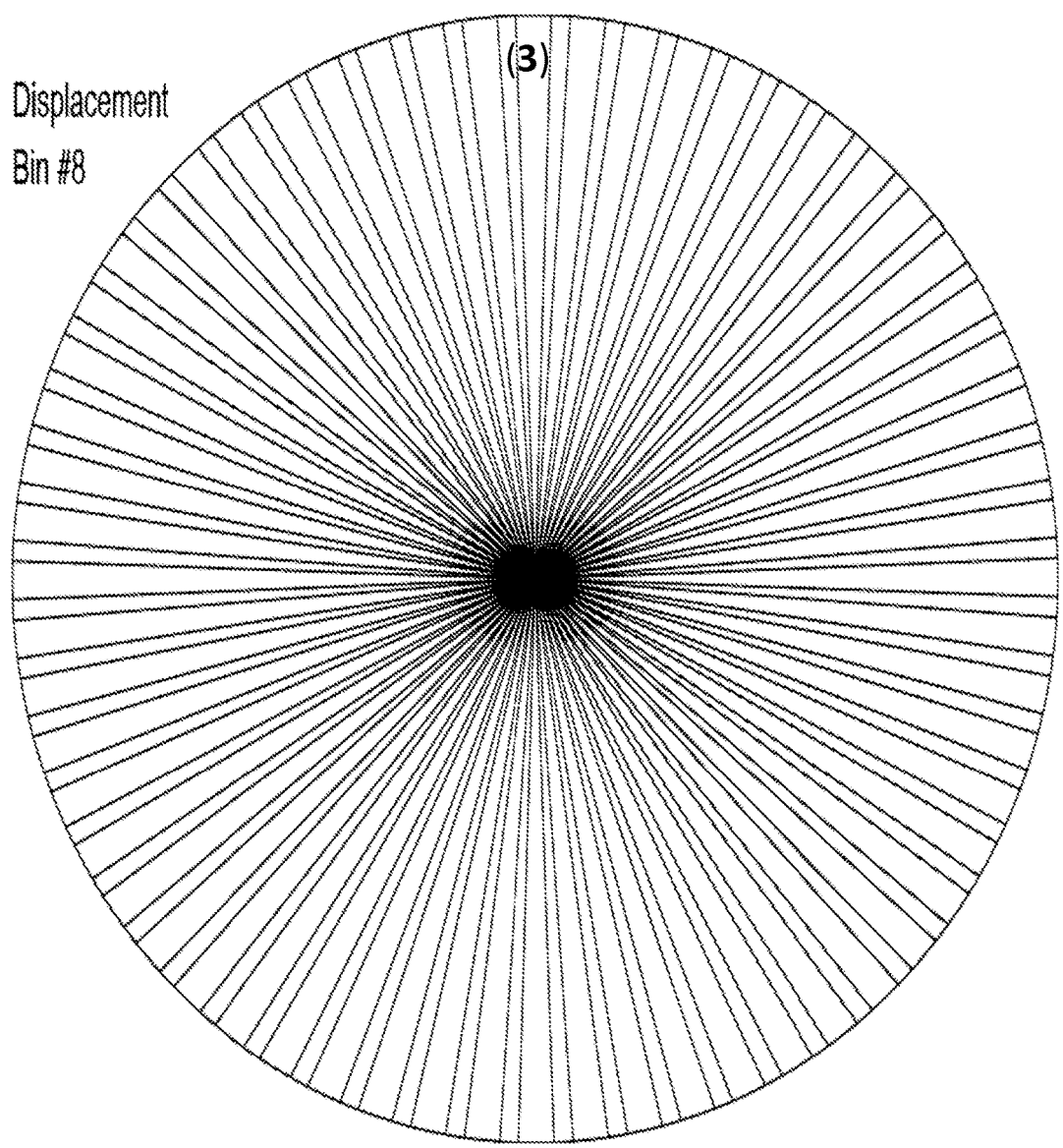

According to one embodiment of the current invention, RMG-4DCBCT improves the angular separation of projections in each respiratory bin during 4DCBCT imaging. That is, the invention makes the polar plots in each respiratory bin more like the plot shown in FIG. 2a than the plot shown in the polar plot of FIG. 2c.

To do this, two additional degrees of freedom are used over current generation 4DCBCT methods.

The first degree of freedom is that rather than moving the gantry with a constant angular velocity the motion of the gantry is allowed to be regulated within the motion of the gantry is regulated within specified limits, where the limits can include minimum and maximum velocity, minimum and maximum acceleration, minimum and maximum jerk, minimum and maximum time between projections, minimum and maximum number of projections, minimum and maximum number of projections per respiratory bin, maximum imaging radiation dose, minimum and maximum image quality, minimum and maximum probability on the robustness of the schedule to irregular breathing, minimum and maximum likelihood of reconstructing a suitable schedule when the patients breathing becomes irregular, minimum and maximum number of respiratory bins and total imaging time.

The second degree of freedom is that rather than using a constant projection pulse rate of 0.2 seconds, the time interval between projections is varied.

Figure 4:
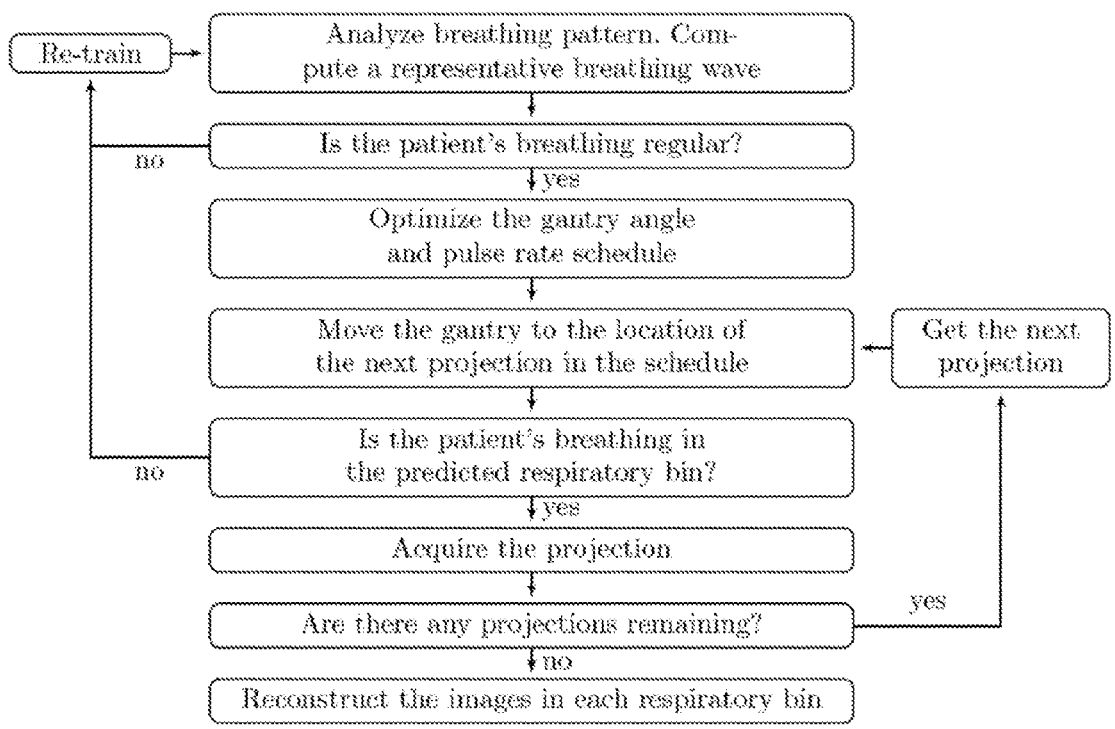
FIG. 4 shows a flow diagram of the system that implements RMG-4DCBCT using a breathing trace to optimize the projection schedule by regulating the gantry angle and projection pulse rate, according to one embodiment of the invention.

The current invention includes a system that implements RMG-4DCBCT using a breathing trace to optimize the projection schedule by regulating the gantry angle and projection pulse rate. A flowchart of the process is given in FIG. 4. The patient's breathing pattern is analyzed and a representative breathing cycle is determined. The representative breathing cycle is used to compute a gantry angle and projection pulse rate schedule using MIQP techniques. If the patient's breathing becomes irregular, acquisition is stopped, then the patient's breathing is allowed to settle down, a new schedule is recomputed and acquisition is continued. It is therefore important to be able to quickly re-compute a projection schedule as any delays increase the imaging time, and discomfort, to the patient. Ideally, this would take less than one second, but the length of a breathing cycle, typically 4 seconds, is acceptable.

There have been some attempts to determine if breathing is irregular or if it is chaotic. In either case, if breathing is irregular or chaotic, it is very difficult to predict a patient's breathing for one or two cycles ahead. Predicting a patient's breathing for the entire duration of a CBCT scan is even more difficult. To overcome the problems associated with irregular breathing, audio and visual queues are used to guide the patient's breathing.

These systems typically monitor external markers on a patient's abdomen to provide near real-time data on the patient's breathing. A representative breathing wave is computed during a training phase and then the patient attempts to follow the representative breathing wave with both audio and visual queues. For most patients, this makes their breathing more regular and easier to predict.

In order to reduce artifacts in CBCT images, respiratory bins are used which have a negligible anatomic motion. For example, one respiratory bin might be at exhale limit, another at inhale limit with several bins dividing the region between inhale and exhale limits. The bins can be based either on displacement of the lungs or abdomen as measured by an external system, or breathing phase which can also be obtained from the RPM system.

Once the patient's representative breathing wave is obtained, it is used to compute a set of time windows, $R_{b,j}$, which define the estimated entry and exit times for each respiratory bin:

$$R_{b,j} = \{ts_{b,j}, te_{b,j}\} \text{ for } b=1,2,\ldots,N \text{ and } j=1,\ldots,N_b, \quad (1)$$

where b is the $b^{th}$ respiratory bin, j is the $j^{th}$ time that the patient's breathing has entered respiratory bin b, $ts_{b,j}$ is the start or entry time for the time window, $te_{b,j}$ is the exit time for the time window, $N_b$ is the number of time windows for bin b and N is the number of respiratory bins.

The time windows are computed numerically in a pre-processing stage before image acquisition starts. Projections taken between $ts_{b,j}$ and $te_{b,j}$ must be allocated to respiratory bin b and used to reconstruct the image for respiratory bin b.

By assuming that the time interval between projections, $\Delta t_k$, is to be determined as part of the optimization and a projection is taken at time $t_k$, then the following equations and constraints governing time are given by:

$$t_{k+1} = t_k + \Delta t_k \text{ for } k=1,2,\ldots,M,$$

$$\Delta t_k \geq \Delta t_{min} \text{ for } k=1,2,\ldots,M,$$

where $M = \Sigma_{b=1}^N M_b$ is the total number of projections taken, $M_b$ is the number of projections taken in respiratory bin b and $t_M = t_{max}$ is the total image acquisition time. The minimum time, $\Delta t_{min}$, is the minimum time required for the detector to be ready to record a second projection after taking a projection. This is an input into the optimization and needs to be measured for each CBCT device. A value of $t_{min} = 0.1$ seconds is realistic for current generation systems.

If the time span between projections is constant, then the projections can be assigned to respiratory bins in a pre-processing phase. Unfortunately, assigning projections to respiratory bins is much more difficult when the time span between projections is a decision variable. To determine the respiratory bin that the projection taken at time $t_k$ belongs, binary variables $\delta_{b,j,k}$ are introduced, which take the value 1 if $t_k$ is in time window $R_{b,j}$ and zero otherwise:

$$ts_{b,j}\delta_{b,j,k} \leq t_k \leq te_{b,j} + (1-\delta_{b,j,k})t_{max} \text{ for all } b, j \text{ and } k.$$

$$\sum_{b=1}^{N}\sum_{j=1}^{N_b} \delta_{b,j,k} = 1 \text{ for all } k,$$

$$\sum_{j=1}^{N_b} \delta_{b,j,k} = \delta_{b,k} \text{ for all } b \text{ and } k.$$

where $\delta_{b,k}$ is 1 if the projection taken at time $t_k$ is in respiratory bin b and zero otherwise.

There are several constraints related to the motion of the gantry that must be applied. The gantry can only rotate between 0° and 360°. When the gantry hits either 0° or 360° it must stop or change direction. Let $\theta_k$ be the position of the gantry for the projection taken at time $t_k$, then the limits on the gantry angle can be modeled with:

$$0 \leq \theta_k \leq 2\pi \text{ for all } k.$$

For full fan acquisition the gantry can rotate from 0° to 180°, plus the fan angle, ω, so $$0 \leq \theta_k \leq \pi+\omega \text{ can be applied for all } k:$$

Physically, the gantry has mechanical constraints on maximum velocity and maximum acceleration.

The maximum velocity in the clockwise direction, $\dot{\theta}_{max}$, can be different to the maximum velocity in the anticlockwise direction, $\dot{\theta}_{max}$. However, for safety reasons, current generation linear accelerators are limited to 6°/s. The maximum velocity constraint is modeled with $$-\dot{\theta}_{max}\Delta t_k \leq \theta_{k+1}-\theta_k \leq \dot{\theta}_{max}\Delta t_k \text{ for all } k. \quad (2)$$

Maximum acceleration, $\ddot{\theta}_{max}$, and deceleration, $\ddot{\theta}_{max}$, are influenced by gravity and other mechanical constraints with the values varying with gantry angle. Values for acceleration have been measured at between 1.8°/s² and 3.2°/s², with deceleration measured at between 3.4°/s² and 4.3°/s² for the Elekta Synergy linear accelerator. In this example, to simplify the model, the acceleration is assumed to be constant for all gantry angles. The acceleration is modeled by fitting a polynomial to three consecutive gantry angles and differentiating twice:

$$-\ddot{\theta}_{max}(\Delta t_{k-1}^2 \Delta t_k + \Delta t_k^2 \Delta t_{k-1}) \leq 2(\theta_{k+1}-\theta_k)\Delta t_{k-1} - 2(\theta_k-\theta_{k-1})\Delta t_k$$
$$\leq \ddot{\theta}_{max}(\Delta t_{k-1}^2 \Delta t_k + \Delta t_k^2 \Delta t_{k-1}) \text{ for all } k.$$

Successive Linear Programming (SLP) is used to handle the acceleration constraint.

To model the objectives of assigning gantry angles to respiratory bins the Mb gantry angles in each respiratory bin need to be in increasing order. An assignment, or bipartite matching, formulation is chosen to order the gantry angles. In each respiratory bin, b, let $\theta_{b,l}$ be the ordered gantry angles with $$\theta_{b,l+1} \geq \theta_{b,l} \text{ for all } b \text{ and } l=1,2,\ldots,M_b.$$

Binary variables $x_{b,k,l}$ are introduced that take the value 1 if $\theta_k$ is the $l^{th}$ largest gantry angle in respiratory bin b and zero otherwise:

$$\sum_{k=1}^{M} \theta_k x_{b,k,l} = \theta_{b,l} \text{ for all } b \text{ and } l, \quad (3)$$

$$\sum_{k=1}^{M} x_{b,k,l} = 1 \text{ for all } b \text{ and } l,$$

$$\sum_{l=1}^{M_b} x_{b,k,l} = 1 \text{ for all } b \text{ and } k.$$

$$x_{b,k,l} \leq \delta_{b,k} \text{ for all } b, l \text{ and } k.$$

Note that in equation (3) the product of a continuous and binary variable is provided. The following technique to linearize the product is used. Let x be a binary variable and $0 \leq y \leq y_{max}$ be a continuous variable, then the product z=xy can be linearized with the following three constraints $$z \leq y_{max}; z \leq y \text{ and } z \geq y-(1-x)y_{max}.$$

According to the invention, there are several objectives that could be used:
1. Minimize the time required to acquire a set of projections with a specified angular separation between the projections.
2. Given that Mb projections are taken per respiratory bin, minimize the Root Mean Squared (RMS) of the angular separation between the projections. This will also require an additional constraint on the time to collect the projections.
3. Maximize a function that represents the quality of the images produced subject to additional constraints on the number of projections taken. For example, we might be able to develop a metric for the quality of an image.

In the case of minimizing the time required to acquire the projections, the objective is $$\text{minimize } t_M = t_{max} \quad (4)$$

However, additional constraints need to be specified to guarantee that sufficient projections are collected for image reconstruction. If $M_b$ projections per respiratory bin are taken, with an angular separation of exactly $\Delta\theta_b=2\pi/M_b$ ($\Delta\theta_b=(\pi+\omega)/M_b$ for full fan acquisition), then $$M_b = \sum_{k=1}^{M}\sum_{j=1}^{N_b} \delta_{b,j,k} \text{ for all } b, \quad (5)$$

$$\Delta\theta_b = \theta_{b,l+1} - \theta_{b,l} \text{ for } l=1, 2, \ldots, M_b - 1, \quad (6)$$

$$\Delta\theta_b = 2\pi - (\theta_{b,M_b} - \theta_{b,0}) \text{ for half fan acquisition.} \quad (7)$$

$$\Delta\theta_b = \pi + \omega - (\theta_{b,M_b} - \theta_{b,0}) \text{ for full fan acquisition.}$$

Alternatively a range for the gantry angles can be introduced by replacing equations (6) and (7) with $$l\Delta\theta_b - \epsilon \leq \theta_{b,l} \leq l\Delta\theta_b + \epsilon \text{ for all } l,$$

where ϵ is an allowable tolerance on the ideal gantry angle.

For minimizing the RMS of the angular separation between projections, the ideal angular separation between projections is $\Delta\theta_b=2\pi/M_b$. The RMS of the separation between consecutive projections in bin b is given by $$RMS_b^2 = \quad (8)$$
$$\left[\sum_{l=1}^{M_b-1}(\theta_{b,l+1}-\theta_{b,l}-\Delta\theta_b)^2 + (2\pi-(\theta_{b,M_b}-\theta_{b,0})-\Delta\theta_b)^2\right]/M_b$$

for all b.

and the objective can be written as $$\text{Minimize} \sum_{b=1}^{N} RMS_b^2. \quad (9)$$

This is a quadratic objective and can be solved with the quadratic solvers in most commercial optimization packages. As an alternative, the RMS could be minimized from the ideal gantry angles $$RMS_b^2 = \left[\sum_{l=1}^{M_b} (\theta_{b,l} - l\Delta\theta_b)^2\right] / M_b \text{ for all } b.$$

For full fan acquisition $\Delta\theta_b = (\pi+\omega)/M_b$ is used and replace equation (8) with $$RMS_b^2 = \left[\sum_{l=1}^{M_b-1} (\theta_{b,l+1} - \theta_{b,l} - \Delta\theta_b)^2 + (\pi + \omega - (\theta_{b,M_b} - \theta_{b,0}) - \Delta\theta_b)^2\right] / M_b$$

for all $b$.

For robust optimization, as mentioned previously, breathing is considered to be irregular or chaotic. This is particularly the case for lung cancer patients who typically have difficulties breathing. There will be instances when the optimized projection schedule is impossible to acquire because the patient's breathing pattern has changed. It is therefore important to make sure that if the patient's breathing changes then the time required to collect the missed projections does not significantly increase the image acquisition time.

There has not been a detailed study of patients breathing to assign a probability that breathing will change or to classify the nature of the change. It is therefore difficult to write down constraints that compute a robust projection schedule based on sound probabilistic principles. Instead one, or all, of the following are applied to make the projection schedule 'more' robust:

Avoid taking projections close to the end of the time windows defined by equation (1). If the patient's breathing changes, there is a better chance of acquiring the projection within the allocated time window if there exists some time to spare.

Compute the initial projection schedule with a lower maximum acceleration and velocity than can be achieved in practice. This will allow some capacity to move the gantry faster than planned when acquiring projections.

Compute the initial projection schedule by using a faster breathing cycle. If the patient's breathing slows down, then there is generally no problem as we can still acquire the projections.

Even if the projection schedule is robust there will be instances when a new schedule is required. The time required to re-optimize the projection schedule will increase the total image acquisition time. Ideally, re-optimization should take less than 1 second with one breathing cycle, about 4 seconds, being an upper limit.

The MIQP model has been implemented using the three leading commercial solvers (ILOG CPLEX, XPRESS-MP and GUROBI). The linear relaxation of the problem is poor and all three commercial solvers fail to obtain optimal solutions to problems with any more than a small number of projections and respiratory bins.

Although obtaining a provably optimum solution is difficult, one can make considerable progress by implementing a method to generate an initial feasible solution (The Initialization Heuristic) and a k-opt exchange heuristic. The initialization heuristic has a computation time of under 1 second and can be used in practice to generate both an initial projection schedule and an updated projection schedule whenever a patient's breathing becomes irregular. The k-opt is used to exchange heuristic to assess the accuracy of the initialization heuristic locally.

The heuristic presented in this section is used to generate an initial feasible solution to the MIQP model. The heuristic can be implemented in under 1 second using the barrier method in most Quadratic Programming (QP) solvers.

There are two simplifications to the model that eliminate the decision variables and allow the problem to be solved efficiently. First, if it is assumed that a given number of projections, $K(b, j)$, will be taken in each time window, $R_{b,j}$, then the binary variables are not needed, $\delta_{b,j,k}$, that determine which respiratory bin the projections belong. $K(b, j)$ can be used to determine the time window that projection taken at time $t_k$ belongs and apply $ts(b,j) \leq t_k \leq te(b,j)$ for projection $k$ in respiratory bin $R(b,j)$.

The easiest way to allocate projections to time windows is to evenly distribute the projections across the time windows, $R(b, j)$. That is, take $\lfloor M_b/N_b \rfloor$ projections per time window with the remaining $M_b - \lfloor M_b/N_b \rfloor$ evenly spaced across the time windows. The maximum number of projections per time window can be calculated using $K(b, j) \leq 1 + (te_{b,j} - ts_{b,j})/\gamma t_{min}$. The second simplification eliminates the binary variables, $x_{b,k,l}$, which where used above to order the projections within each respiratory bin. Within each respiratory bin, the gantry is forced to take projections with an increasing gantry angle. That is, the constraint $\theta_{b,j+1} \geq \theta_{b,j}$ is applied for all values of j. This does not restrict the gantry from changing direction between respiratory bins; the condition ensures that consecutive projections within the same respiratory bin are taken in increasing order. Using the notation $M:k \to (b, l)$ which maps a projection, $\theta_k$ taken at time $t_k$, to its corresponding ordered projections $\theta_{b,l}$. That is, M takes a value of k and maps it to a unique pair $(b, l)$ so that $\theta_k = \theta_{b,l}$. Every k must map to a unique pair $(b, l)$ and every $(b, l)$ has a corresponding value of k.

Pseudo code of the method used to initialize M and K is given in algorithm 1. Some k-opt exchange heuristics are introduced below with the aim of modifying the mappings M and K in a way that improves the objective function locally. In order to do this, an efficient way of using M and K is needed to compute the objective function. The pseudo code for the Optimization algorithm is given in algorithm 2.

---

Algorithm 1 Initialize( ).

---

{Initialize $\mathcal{K}$.}
for b = 1 to N do
  n = $\lfloor M_b/N_b \rfloor$; $\delta n = M_b - nN_b$; $\delta j = M_b/\delta n$
  for j = 1 to $M_b$ do
    $\mathcal{K}$ (b, j) = n
  end for
  for i = 1 to $\delta n$ do
    j = $\lfloor (i - 1)\delta j \rfloor$; $\mathcal{K}$ (b, j) = $\mathcal{K}$ (b, j) + 1

-continued

Algorithm 1 Initialize( ).

```
        end for
    end for
{Initialize 𝓜.}
k = 0
for b = 1 to M_b do
    L[b] = 0
end for
Order projection windows 𝒦 (b, j) from lowest
    to highest t, to get 𝒦'(b, j).
for all (b, j) in 𝒦' do
    for i = 1 to 𝒦'(b, j) do
        l = L[b]; 𝓜(k) = (b, l); L[b] = L[b] + 1; k =
            k + 1
    end for
end for
Optimize(𝓜,𝒦)
```

Algorithm 2 Optimize(𝓜, 𝒦).

```
{Check if values exist.}
if Cache Contains(𝓜,𝒦) then
    objective = Cache(𝓜,𝒦)
else
    {Formulate QP by excluding the sections
     modeling the binary variables.}
    for k = 1 to M do
        (b, l) = 𝓜(k)
        Add constraint θ_{b,l} = θ_k
    end for
    k = 1
    for b = 1 to N do
        for j = 1 to M_b do
            for i = 0 to 𝒦(b, j) do
                Add constraint ts_{b,j} ≤ t_k ≤ te_{b,j}
                k = k + 1
            end for
        end for
    end for
    objective = Solve( ) - using XPRESS-MP,
        CPLEX or GUROBI
    Cache(𝓜,𝒦) = objective
end if
return objective
```

Regarding the k-opt exchange heuristic for the time windows, the mapping 𝒦 contains the number of projections in each time window $R_{b,j}$. The k-opt exchange heuristic swaps projections from one time window to another in a systematic fashion to see if the exchange improves the solution. Algorithm 3 contains pseudo code for the 2-opt exchange heuristic (TimeWindows). For higher order swaps k must be even, and the number of exchanges increases exponentially with k. In the worst case there are $\Sigma_b N_b(N_b-1)$ swaps for the 2-opt exchange heuristic. In practice, k is usually kept small, say 2, or a method where the depth of the exchange can be varied is often used in the traveling salesman literature.

At each stage of the algorithm the current best solution can be examined to identify potential exchanges that are likely to improve the objective value. To do this, the time windows are ordered from those that have the highest clustering of projections to the time windows with the least clustered projections. Start the algorithm by taking a projection from the most clustered time window and putting the projection in the least clustered time window. A solution is considered k-optimal if there is no combination of k swaps that improve the solution. To obtain a k-optimal solution multiple passes of the k-opt exchange heuristic are required until there are no changes made. In the pseudo code in algorithm 3 the solution is 2-optimal if the variable exchanges is zero after the TimeWindows algorithm has finished. In most practical situations, the objective is improved more in the first few passes of the k-opt algorithm than in later passes. It is usually beneficial to terminate the search after the first few passes rather than doing excessive amounts of work for a small improvement to the solution.

Algorithm 3 TimeWindows(𝓜, 𝒦). The 2-opt exchange heuristic for the time windows.

```
exchanges = 0
for b = 1 to N do
    for j1 = 1 to N_b do
        for j2 = 1 to N_b, j_2 ≠ j_1 do
            𝒦' = 𝒦
            𝒦'(b, j_1) = 𝒦'(b, j_1) - 1
            𝒦'(b, j_2) = 𝒦'(b, j_2) + 1
            if 𝒦'(b, j_1) ≥ 0 and GantryAngles(𝓜,
                𝒦') < GantryAngles(𝓜, 𝒦) then
                𝒦 = 𝒦'
                exchanges = exchanges + 1
            end if
        end for
    end for
end for
return 𝒦
```

Algorithm 4 GantryAngles(𝓜,𝒦). The 2-opt exchange heuristic for the gantry angles.

```
exchanges = 0
for k_1 = 1 to M do
    (b_1, l_1) = 𝓜(k_1)
    for k_2 = k_1 + 1 to M do
        (b_2, l_2) = 𝓜(k_2)
        if b_1 == b_2 then
            𝓜' = 𝓜; temp = 𝓜'(k_1)
            𝓜'(k_1) = 𝓜'(k_2); 𝓜'(k_2) = temp
            if Optimize(𝓜', 𝒦) < Optimize(𝓜,𝒦)
                then
                𝓜 = 𝓜';
                exchanges = exchanges + 1
            end if
        end if
    end for
end for
return Optimize(𝓜,𝒦)
```

Regarding the k-Opt exchange heuristic for the gantry angles, the algorithm below is similar to that used above. Start with an ordering of the projections 𝒦 and then swap k projections. The resulting QP is optimized and the exchange is accepted if the objective is better. Algorithm 4 gives pseudo code for the 2-opt exchange heuristic applied to the gantry angles.

The maximum acceleration of OBI's on the current generation of linear accelerations is not high, typically $1.8°/s^2$, so the GantryAngles algorithm is less likely to improve the solution than the TimeWindows algorithm. The GantryAngles algorithm is therefore applied after an improved solution has been found by the TimeWindows algorithm.

Regarding the Constant Angular Velocity (CAV) Algorithm, current generation 4DCBCT techniques are based on a constant angular velocity of the gantry, with a constant projection pulse rate. To generate the data using a constant angular velocity, only one rotation of the gantry is used. The velocity of the gantry is given by dividing 360° by the imaging time. For example, if the imaging time is 240 seconds then the velocity of the gantry is 1.5°/s. Similarly, the projection pulse rate can be determined by dividing the image time by the total number of projections (projections per bin multiplied by the number of respiratory bins). For example, if 10 respiratory bins are used with 120 projections per bin then the projection pulse rate is 0.2 seconds.

Only the initialization heuristic has a computation time that is fast enough to implement in practice. It is desired to determine parameter settings where the initialization heuristic is close to optimal and where improvements are required. The 2-opt exchange heuristic can be used to explore the solution space within a small neighborhood of the solution obtain from the initialization heuristic. If the 2-opt exchange heuristic produces a significantly better solution then it can be concluded that the initialization heuristic is less than optimal for the parameter settings used and further algorithm development is required.

Even if projection clustering occurs, the objective value can be expected, as defined by equation 9, to get smaller as more projections are taken in each respiratory bin. Therefore one can scale equation 9 to give the scaled objective $$\text{Scaled objective} = 100 \left[ \sum_{b=1}^{N} RMS_b^2 / (\Delta\theta_b^2 N) \right]^{1/2}.$$

A scaled objective of zero means that there is perfect angular spacing of the projections. A scaled objective of 100 means that the standard deviation between projections is $\Delta\theta_b$; i.e. one is likely to see two, or more, projections with a similar gantry angle followed by a gap of approximately $2\Delta\theta_b$.

In the numerical experiments the default, or baseline, settings are 120 projections per respiratory bin, 10 respiratory bins (i.e. 1200 projections in total), the projections are taken over 240 seconds, the maximum gantry acceleration is 1.6°/s$^2$ and the maximum gantry velocity is 6°/s. The default settings represent the capabilities of the OBI's on current generation linear accelerators.

Comparisons of the scaled objective from the initialization heuristic and the 2-opt exchange heuristic are given in Table 1 for both displacement and phase binning. The 2-opt exchange heuristic on the gantry angles was applied only to the final solution from the 2-opt TW column. Using the default settings one finds that there is no significant improvement to the solution after applying the 2-opt exchange heuristics. That is, the initialization heuristic computes a solution that is near optimal locally. Similarly, if the gantry velocity or acceleration is increased, but retain 120 projections per respiratory bin, the 2-opt exchange heuristic does not find an improved solution when compared to the initialization heuristic.

When the average time between projections is increased, the 2-opt exchange heuristic on the time windows finds better solutions than the initialization heuristic. This can be observed in the last three rows of Table 1 which correspond to 50 projections per bin and 200 seconds imaging time. The first 9 rows in Table 1 have the same average time between projections, 0.2 seconds, and the 2-opt exchange heuristic does not find an improved solution. However, the last three rows have an average time of 0.4 seconds between projections and the 2-opt exchange heuristic has found improved solutions. An explanation for these results is that, with displacement binning, one projection is taken in each time window when 120 projections are taken per respiratory bin over 240 seconds. When the average time between projections is increased to 0.4 seconds, a projection is taken on average every second time window. The 2-opt exchange heuristic improves the allocation of projections to time windows and, in particular, does better at selecting the time windows that do not have a projection allocated.

TABLE 1

The scaled objective value with the initialization heuristic from algorithm 1 (Initialize), the 2-opt exchange heuristic on the time windows from algorithm 3 (2-opt TW) and the 2-opt exchange heuristic on the gantry angles from algorithm 4 (2-opt-GA). In all simulations it was assumed that the patient was breathing at 15 hz and there are 10 respiratory bins.

| Projections per bin | Imaging time | Maximum | | Displacement Binning | | | Phase Binning | | |
|---|---|---|---|---|---|---|---|---|---|
| | | Vel °/s | Acc °/s$^2$ | Initialize | 2-opt TW | 2-opt GA | Initialize | 2-opt TW | 2-opt GA |
| 120 | 240 | 6 | 1.8 | 21.2 | 21.2 | 21.2 | 84.1 | 84.1 | 84.1 |
| 120 | 240 | 30 | 3 | 12.3 | 12.3 | 12.3 | 83.5 | 83.5 | 81.6 |
| 120 | 240 | 30 | 6 | 2.0 | 2.0 | 2.0 | 82.0 | 79.2 | 73.2 |
| 100 | 200 | 6 | 1.8 | 23.8 | 23.8 | 23.8 | 84.3 | 84.3 | 84.3 |
| 100 | 200 | 30 | 3 | 16.4 | 16.4 | 16.4 | 83.8 | 83.7 | 83.6 |
| 100 | 200 | 30 | 6 | 5.5 | 5.5 | 5.5 | 82.5 | 79.0 | 78.9 |
| 50 | 100 | 6 | 1.8 | 29.9 | 29.9 | 29.9 | 84.6 | 84.6 | 84.6 |
| 50 | 100 | 30 | 3 | 26.0 | 26.0 | 26.0 | 84.4 | 84.4 | 84.4 |
| 50 | 100 | 30 | 6 | 16.9 | 16.9 | 16.9 | 83.8 | 83.8 | 83.8 |
| 50 | 200 | 6 | 1.8 | 2.4 | 0.2 | 0.2 | 0.1 | 0.1 | 0.0 |
| 50 | 200 | 30 | 3 | 1.5 | 1.2 | 1.2 | 0.1 | 0.0 | 0.0 |
| 50 | 200 | 30 | 6 | 0.1 | 0.0 | 0.0 | 0.0 | 0.0 | 0.0 |

It should be noted that although the initialization heuristic performs well in most cases, the above results suggest that the 2-opt exchange heuristic is likely to find better solutions when the number of projections in each time window are not the same. In practice, 120 projections per respiratory bin and an imaging time of 240 seconds is common, so the initialization heuristic is likely to have good performance.

The 2-opt exchange heuristic on the gantry angles improves the solution when the acceleration is high and a large number of projections are taken. This is particularly evident in the third row of Table 1 where exactly two projections are taken per respiratory bin. Under these circumstances the gantry is frequently changing direction in order to collect the projections. A higher value of k in the k-opt search may also find improved solutions. For current generation linear accelerators, an acceleration of 6° is not possible.

To examine the performance of the initialization heuristic compared to the CAV algorithm for both current and future generation systems, simulations have been run with a maximum velocity of 6, 10, 15 and 30°/s, and a maximum acceleration of 1.8, 3, 6 and 12°/s$^2$. Simulations were run where the total number of projections have been reduced to as low as 50 projections per respiratory bin. Tables comparing the results with the initialization heuristic to current CAV 4DCBCT techniques are given in Table 2.

TABLE 2

The scaled objective for the CAV algorithm (CAV algorithm) and initialization heuristic (Initialize). Results with * indicate that not all respiratory bins had the same number of projections.

| Respiratory Rate (hz) | Bins | Maximum Vel °/s | Acc °/s$^2$ | Projections per bin | Imaging time | Displacement Binning CAV algorithm | Initialize | Phase Binning CAV algorithm | Initialize |
|---|---|---|---|---|---|---|---|---|---|
| 15 | 10 | 6 | 1.8 | 120 | 240 | 90.9* | 21.2 | 90.0 | 84.1 |
| 15 | 10 | 6 | 3 | 120 | 240 | 90.9* | 12.3 | 90.0 | 83.5 |
| 15 | 10 | 6 | 6 | 120 | 240 | 90.9* | 2.0 | 90.0 | 82.0 |
| 15 | 10 | 6 | 12 | 120 | 240 | 99.9* | 0.3 | 90.0 | 78.5 |
| 15 | 10 | 10 | 1.8 | 120 | 240 | 90.9* | 21.2 | 90.0 | 84.1 |
| 15 | 10 | 15 | 1.8 | 120 | 240 | 90.9* | 21.2 | 90.0 | 84.1 |
| 15 | 10 | 30 | 1.8 | 120 | 240 | 90.9* | 21.2 | 90.0 | 84.1 |
| 15 | 4 | 6 | 1.8 | 120 | 240 | 132.6* | 7.6 | 150.0 | 52.4 |
| 15 | 6 | 6 | 1.8 | 120 | 240 | 122.1* | 14.9 | 127.9 | 70.0 |
| 15 | 8 | 6 | 1.8 | 120 | 240 | 107.7* | 18.5 | 109.1 | 78.8 |
| 10 | 10 | 6 | 1.8 | 120 | 240 | 120.7* | 70.1 | 127.3 | 123.1 |
| 18 | 5 | 6 | 1.8 | 120 | 240 | 111.2* | 14.0 | 73.5 | 70.8 |
| 30 | 5 | 6 | 1.8 | 120 | 240 | 76.7* | 0.6 | 0.0 | 0.0 |
| 15 | 10 | 6 | 1.8 | 60 | 120 | 90.9* | 28.2 | 90.0 | 84.6 |
| 15 | 10 | 6 | 1.8 | 200 | 400 | 90.9* | 12.7 | 90.0 | 83.5 |
| 15 | 10 | 6 | 1.8 | 120 | 160 | | | 127.3 | 113.5 |
| 15 | 10 | 6 | 1.8 | 120 | 180 | | | 116.2 | 102.9 |
| 15 | 10 | 6 | 1.8 | 120 | 200 | | | 108.9 | 84.8 |

The initial discussion focuses on the displacement binning results where increasing the maximum gantry acceleration from 1.6°/s$^2$ to 12°/s$^2$ improves the scaled objective value from 21.2 to 0.3 with the initialization heuristic while the CAV algorithm has a scaled objective of 90. Increasing the maximum velocity of the gantry to 30°/s does not improve the solution. An explanation is that the gantry makes only one rotation with an average angular velocity of 1.5°/s. Even if the gantry accelerates and decelerates it does not go above 6°/s. These results clearly show that increasing the maximum acceleration of the gantry is more important than increasing the maximum velocity of the gantry. This is an important result as the gantry on current systems is limited to 6°/s for safety reasons and not mechanical reasons; the results suggest that there is no significant benefit in increasing the maximum velocity.

The rows corresponding to 4, 6 and 8 respiratory bins show that the CAV algorithm gives a higher scaled objective with less respiratory bins while the initialization heuristic has a lower scaled objective. The initialization heuristic performs much better than the CAV algorithm in these cases. When a patient breaths slower, e.g. at 10 hz, the scaled objective for both the CAV algorithm and initialization heuristic are worse than the default breathing rate of 15 hz. For fast breathing patients, with a breathing rate of 18 hz or 30 hz, the scaled objective is lower than the 15 hz case. However, it should be noted that the number of respiratory bins has been reduced in the 18 hz and 30 hz cases. If the number of respiratory bins is not reduced then the length of each time window is shorter and the CAV algorithm misses respiratory bins. It should also be noted that in all cases where the breathing rate differs from 15 hz, the number of projections in each time window are not the same and the 2-opt exchange heuristic is likely to find a better solution than the initialization heuristic.

Increasing the number of projections to 200 with an imaging time of 400 seconds, or decreasing the number of projections to 60 with an imaging time of 120 seconds, has the same average time between projections, 0.2 seconds, as the default case. However, using the initialization heuristic, one finds the scaled objective is smaller as the number of projections is increased.

When phase based binning is used the results follow a similar pattern, but the improvement of the initialization heuristic over the CAV algorithm is not as significant as the displacement binning results. For the default case, with displacement binning, only one projection per time window is required for all bins except the time windows at inhale and exhale limit. In comparison, two projections must be taken, in a short time period, in each time window when phase based binning is used. Only one gantry rotation is allowed with the initialization heuristic so the velocity of the gantry is low, on average 1.5°/s, and the angular separation between the two projections is small with phase based binning.

When the patient is breathing at 30 hz, and phase based binning is used, a constant angular gantry velocity is optimal. In this case, one projection per time window is required and a constant angular velocity of 1.5°/s positions the gantry in an ideal position to take the next projection when the patient's breathing re-enters the respiratory bin. However, in practice, due to irregular breathing, it is unlikely that a patient would be able to maintain a perfect sinusoidal breathing pattern at 30 hz.

Attempting to collect 120 projections in a time period less than 240 seconds will make projection clustering worse. By examining shorter time periods in the last three rows in Table 2, the results show that reducing the imaging time to 200 seconds does not significantly increase the scaled objective over the default, 240 second, imaging time. However, reducing the imaging time to 180 seconds, or less, results in a moderate increase in the scaled objective.

The results indicate that displacement binning is likely to produce better angular separation between projections, and hence better quality images, than phase based binning. However, several practical considerations need to be addressed before this claim can be verified. These include the shorter time period spent in the respiratory bins in the middle of the breathing phase, the corresponding difficulties attempting to take a projection in a smaller time window, problems associated with collecting missed projections in the inhale or exhale respiratory bins if a patient takes a shallow breath and issues with the baseline drift in the displacement signal.

A new MIQP model has been presented for RMG-4DCBCT. Solving the full MIQP model to optimality using the leading commercial MIQP solvers is currently not possible, so an initialization heuristic has been developed that can generate a near optimal feasible solution in under one second. To determine the optimality of the initialization heuristic locally, a 2-opt exchange heuristic was used to show that the initialization heuristic produces a good solution for current generation CBCT devices that are used in radiotherapy.

It was shown that the initialization heuristic significantly improves the angular separation of projections over the CAV algorithms when displacement binning is used with moderate improvement for phase based binning. A second feature of the initialization heuristic is that it is able to re-compute a new projection schedule when a patient's breathing becomes irregular. This is the first 4DCBCT algorithm that can adjust to a patient with irregular breathing.

The optimization model presented, together with the final implementation of RMG-4DCBCT on clinical systems, has the potential to improve the survival outcome and quality of life for lung cancer patients. There has been rapid growth in the use of IGRT and 4DCT by radiotherapists in the past 10-20 years. As 4DCT is not available in the treatment room, and can only be used in treatment planning, RMG-4DCBCT provides a promising method that will allow radiotherapists to position a lung cancer patient for treatment. Consequently, the margins that are added around the tumor to allow for setup errors and patient positioning errors can be reduced; increasing the radiation dose to the tumor and reducing the radiation dose to the surrounding healthy tissue.

Figures 5A, 5B:
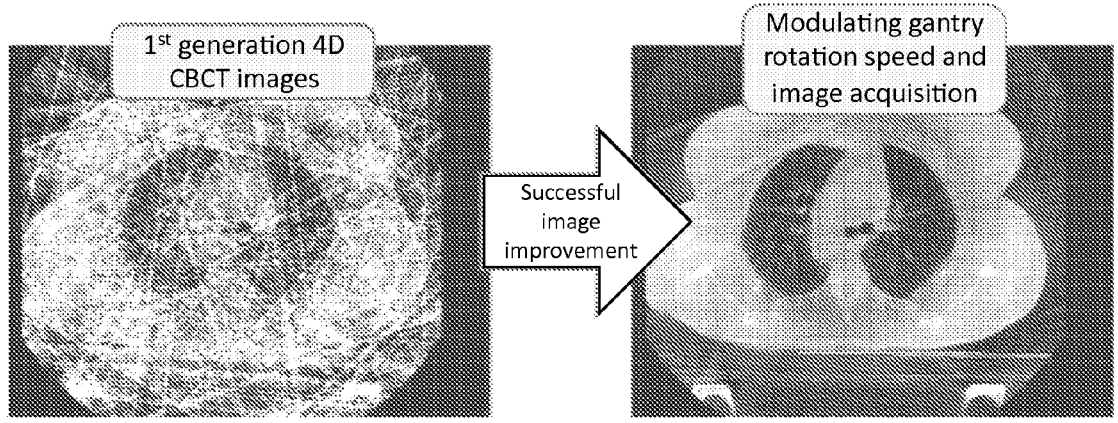
FIG. 5a-5b shows improvement in image quality for equivalent dose comparing 4D CBCT acquisition methods of the current invention, with that achievable by modulating gantry rotation speed and image acquisition.

Exemplary data on image quality improvement is provided, where FIGS. 5a-5b show improvement in image quality for equivalent dose comparing current 4D CBCT acquisition methods (FIG. 5a) with that achieved by modulating gantry rotation speed and image acquisition, according to the current invention (FIG. 5b).

According to one aspect of the invention, RMG 4D-CBCT enables (1) identifying and targeting primary lung tumors and positive nodes, (2) identifying and avoiding critical structures, (3) reducing false positives and false negatives during image interpretation, (4) improving rigid and deformable registration algorithm performance to facilitate online corrections and adaptive radiotherapy strategies, (5) reducing margins and (6) facilitating online functional avoidance through CT-ventilation imaging procedures.

CBCT integrated with a linear accelerator is a powerful tool for image-guided radiotherapy. It allows volumetric imaging of the patient prior to treatment to facilitate aligning the radiation beam with the tumor. 4D CBCT is used to determine the mean position, trajectory and shape of a moving tumor just prior to treatment. This reduces respiration induced geometrical uncertainties, potentially enabling safe delivery of 4D radiotherapy, such as gated radiotherapy, with small margins.

Figure 6:
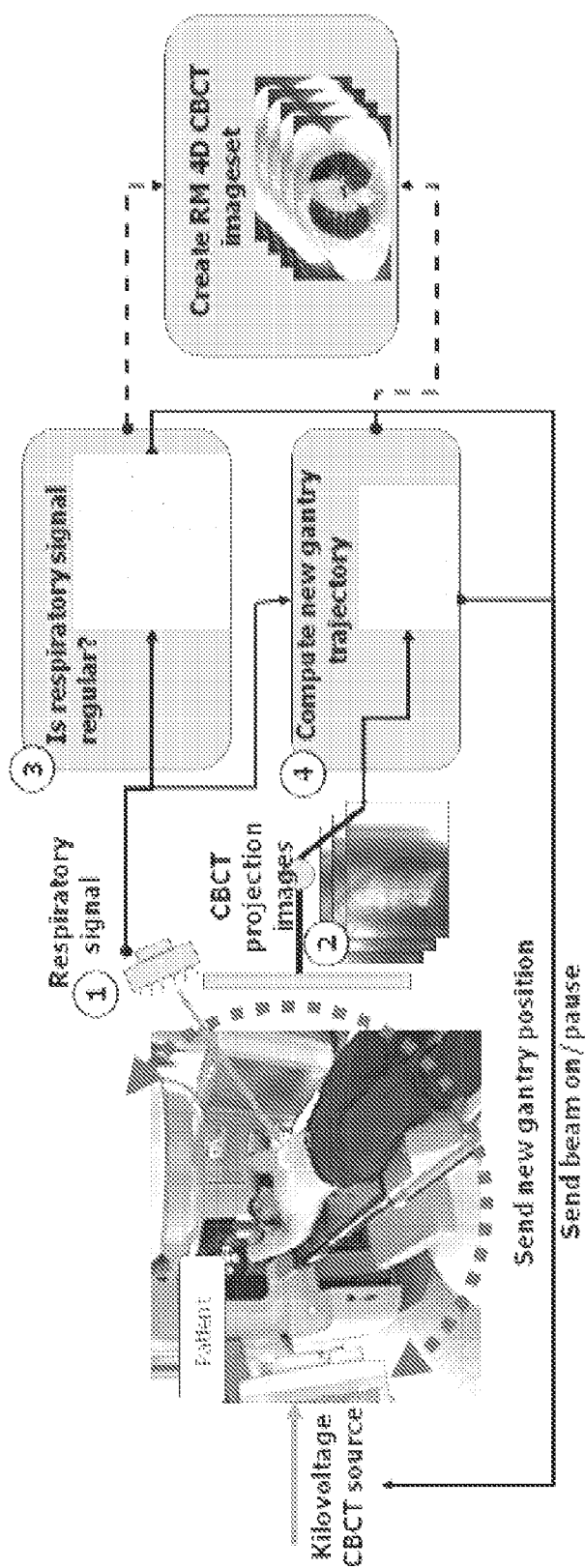
FIG. 6 shows a schematic of the RMG 4DCBCT method in which the respiratory signal is actively used to modulate gantry rotation and image acquisition, according to one embodiment of the current invention.

According to one embodiment of the invention, an RMG 4D-CBCT method is shown schematically in FIG. 6. The respiratory signal (1) and the projection images (2) are input into the two main computational tasks to determine if the respiratory signal is regular (3) and to compute the new gantry trajectory (4). The new gantry position signal and beam on/pause signal is then fed back in real time to the image acquisition system.

In one aspect of the invention, computational tasks are to determine if the respiratory signal is regular (box 3 in FIG. 6) and to compute the new gantry trajectory (box 4 in FIG. 6).

The method is used to determine if the respiratory signal is regular for improving 4D CT images. Tolerance values for variability in the breathing displacement period are input, then adapted as necessary to ensure sufficient images are acquired for reconstruction.

According to one embodiment, to compute the new gantry trajectory (box 4 in FIG. 6) the problem is defined as the optimization problem as discussed above. The estimate of the respiratory signal, and therefore the optimal gantry trajectory at increasing time becomes increasingly inaccurate. However, this calculation needs to be repeated as every new respiratory signal or projection is input, so the estimate of the optimal gantry angle trajectory is constantly updated when new information is available.

The image reconstruction occurs as a separate process to the image acquisition. For this task Exxim's Cobra implementation of the Feldkamp-Davis-Kress (FDK) algorithm for 3D CBCT reconstruction is used, according to one embodiment. Cobra was used to create the images in FIG. 5a-5b.

According to one aspect of the invention, suitable databases are required, for example some suitable databases include:

Synchronous tumor and respiratory motion data from 143 treatment fractions of 42 abdominal and thoracic lung cancer patients.

Respiratory motion data from repeat sessions with and without audiovisual biofeedback for 24 lung cancer patients. The audiovisual system has been shown to reduce baseline shifts, which may improve the efficacy of both 4DCBCT and RMG-4DCBCT.

Using application-specific software for the RMG-4DCBCT, the image acquisition parameters are optimized using existing phantom image data for which the geometry and composition is known. As an example, two types of phantoms are used: an image quality phantom, CatPhan, and an anthropomorphic phantom, Rando.

In one experimental example of the RMG-4DCBCT (FIG. 6), the RMG-4DCBCT software system is integrated by taking the gantry angle reading as input and implementing a device to control gantry rotation. To actualize the motion for the experimental implementation of RMG-4DCBCT, a 4-axis programmable motion phantom is used in one embodiment. This phantom allows programmable and synchronous 1D respiratory signal and 3D tumor motion to be actuated.

The RMG-4DCBCT method utilizes the respiratory signal to modulate the acquisition to ensure image quality and data sufficiency. According to various embodiments, RMG-4DCBCT enables:

1. Identifying and targeting primary lung tumors and positive nodes during treatment.
2. Identifying and avoiding critical structures during treatment.
3. Reducing false positives and false negatives during image interpretation.
4. Improving rigid and deformable registration algorithm performance to facilitate online corrections and adaptive radiotherapy strategies.
5. Reducing margins, particularly for stereotactic body radiotherapy trials such at the TROG 09.02 CHISEL trial.
6. Facilitating online functional avoidance through CT-ventilation imaging procedures.

In this invention the patient signal is used to modulate the gantry speed and image acquisition to yield images for each phase at a predetermined angular spacing, chosen to balance image quality with radiation dose. Additionally, acquisition can be paused during irregular breathing to further improve image quality at the expense of acquisition time.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. Examples of modifications may include beam pause algorithms where the respiratory signal is monitored and the beam is paused to eliminate clustering of projections by only taking the first projection, modifications to the constraints to change their form but not meaning and modifications to the objective function to change its form but not meaning (e.g. to make it linear, cubic, etc).

All such variations are considered to be within the scope and spirit of the present invention as defined by the following claims and their legal equivalents.

What is claimed:

1. A method of optimizing 4D cone beam computed tomography (4DCBCT) imaging, comprising:
   a. generating by scanner projections of a target in a single half fan acquisition or a single full fan acquisition using an x-ray source, wherein said single half fan acquisition comprises a single 360-degree gantry rotation, wherein said full fan acquisition comprises a single 180-degree gantry rotation plus a fan angle ω;
   b. forming by said scanner a cone beam computed tomography (CBCT) scan of said target from said projections, wherein said CBCT comprises a 3D image of said target; and
   c. controlling by an appropriately programmed computer a modulated rotation speed of said gantry and projection acquisition of said CBCT in real-time according to a measured patient respiratory signal using continuous gantry motion and ungated projection acquisition, wherein said ungated projection acquisition comprises segmenting a breathing cycle into distinct fractions of said breathing cycle, wherein each said distinct fraction of said breathing cycle defines a breathing cycle bin location, wherein two degrees of freedom comprise controlling the motion of said gantry and a varied time interval between said ungated projection acquisition, wherein an image is acquired at each said breathing cycle bin location during said single half fan acquisition or said single full fan acquisition, wherein an angle of said gantry is regulated and a rate of a projection pulse from said x-ray source is regulated in response to said respiratory signal, wherein a set of evenly spaced said scanner projections are obtained in a number of phase bins or in a number of displacement bins during said breathing cycle, wherein in each said breathing cycle bin location, an image is reconstructed from said scanner projections to output a 4D view of the anatomy of said patient, wherein the motion of the lungs of said patient and a tumor of said patient are observed during said breathing cycle, wherein said real-time ungated projection acquisition of said CBCT forms an optimized 4DCBCT.

2. The method of optimizing 4DCBCT imaging of claim 1, wherein a time interval between projections of said CBCT is varied.

3. The method of optimizing 4DCBCT imaging of claim 1, wherein acceleration and a velocity of said gantry are varied.

4. The method of optimizing 4DCBCT imaging of claim 1, wherein a breathing trace is used to optimize a projection schedule.

5. The method of optimizing 4DCBCT imaging of claim 1, wherein said optimized projection schedule comprises regulating a gantry angle and regulating a projection pulse rate.

6. The method of optimizing 4DCBCT imaging of claim 1, wherein said control of said modulated gantry rotation speed and projection acquisition of said 4DCBCT in real-time comprises:
   a. analyzing by sensors a patient's breathing pattern to determine a representative breathing trace;
   b. separating the patients representative breathing trace into a number of phase or displacement based respiratory bins;
   c. determining and applying by mathematical optimization techniques on said computer a gantry angle and a projection pulse rate schedule from said representative breathing cycle;
   d. recomputing by said computer said gantry angle and a projection pulse rate schedule if said patient's breathing deviates from said representative breathing cycle; and
   e. continuing said projection acquisition according to said recomputed gantry angle and projection pulse rate schedule.

7. The method of optimizing 4DCBCT imaging of claim 1, wherein motion of said gantry is regulated within specified limits, wherein said limits are selected from the group consisting of minimum and maximum velocity, minimum and maximum acceleration, minimum and maximum jerk, minimum and maximum time between projections, minimum and maximum number of projections, minimum and maximum number of projections per respiratory bin, maximum imaging radiation dose, minimum and maximum image quality, minimum and maximum probability on the accuracy of the schedule to adhere to an irregular breathing cycle, minimum and maximum likelihood of reconstructing a suitable schedule when a patients breathing becomes irregular, minimum and maximum number of respiratory bins and total imaging time.

8. The method of optimizing 4DCBCT imaging of claim 1, wherein said patient respiratory signal is used to modulate said modulated speed of said gantry and modulate said projection acquisition to yield images for each phase of a breathing trace at a predetermined and optimized angular spacing.

9. The method of optimizing 4DCBCT imaging of claim 8, wherein optimizing said gantry angle comprises operations selected from the group consisting of minimizing the time required to acquire the 4DCBCT projections, minimizing the angular separation between the gantry angles for each projection, minimizing the root mean squared of the angular separation between the projections, maximizing the image quality in each respiratory bin, maximizing a number of images acquired, maximizing a number of respiratory bins, maximizing a likelihood of acquiring suitable quality images when a patients breathing becomes irregular, maximizing a robustness of a schedule, and minimizing a radiation dose to said patient.

* * * * *